(12) United States Patent
Mizutani et al.

(10) Patent No.: US 6,508,796 B2
(45) Date of Patent: Jan. 21, 2003

(54) ABSORBENT ARTICLE

(75) Inventors: Satoshi Mizutani, Kagawa (JP); Tatsuya Tamura, Kagawa (JP); Yuuki Noda, Kagawa (JP)

(73) Assignee: Uni-Charm Corporation, Kawanoe ( * ) Notice: Subject to any disclaimer, the term of this patent is extended or adjusted under 35 U.S.C. 154(b) by 0 days.

(21) Appl. No.: 09/803,767

(22) Filed: Mar. 12, 2001

(65) Prior Publication Data

US 2001/0023343 A1 Sep. 20, 2001

(30) Foreign Application Priority Data

Mar. 14, 2000  (JP) ........................................ 2000-069857

(51) Int. Cl.⁷ ............................................... A61F 13/15
(52) U.S. Cl. ............................ 604/385.04; 604/385.27; 604/385.107; 604/385.28
(58) Field of Search ..................... 604/385.04, 385.101, 604/385.24, 385.27, 385.28, 385.01

(56) References Cited

U.S. PATENT DOCUMENTS 5,931,826 A  *  8/1999  Faulks et al. ............. 604/385.2

FOREIGN PATENT DOCUMENTS

| EP | 0346477 A1 | * | 12/1989 |
| EP | 0750894 | * | 1/1997 |
| EP | 0998893 A2 | * | 5/2000 |
| GB | 2233235 A | * | 1/1991 |
| WO | WO98/31320 | * | 7/1998 |

* cited by examiner

*Primary Examiner*—John J. Calvert
*Assistant Examiner*—Angela J Grayson
(74) *Attorney, Agent, or Firm*—Darby & Darby (57) ABSTRACT

There is disclosed an absorbent article including: a main body; and leakage preventing side walls extending in the longitudinal direction of the main body and lying opposite one another in the widthwise direction of the main body. Each leakage preventing side wall has a raised portion which is joined at a root end onto a liquid-receiving side surface of the main body and raised therefrom to have a free end positioned apart from the liquid-receiving side surface. Each leakage preventing side wall is provided with a first elastically shrinking member for applying an elastic shrinking force along a shrinking action line approaching the free end from the root end as it extends from the two longitudinal end positions of the raised portion of the leakage preventing side wall toward the longitudinally midway position of the leakage preventing side wall.

14 Claims, 7 Drawing Sheets

ABSORBENT ARTICLE

BACKGROUND OF THE INVENTION

1. Field of the Invention

The present invention relates to an absorbent article for absorbing and retaining a liquid waste such as menstrual blood and, more particularly, to an absorbent article having leakage preventing side walls on the two widthwise sides of the liquid-receiving side.

2. Related Art

In the prior art, there have been a variety of absorbent articles including a sanitary napkin, a urine absorbing pad and a disposable diaper. These absorbent articles are demanded, when worn, for absorbing the liquid waste reliably in liquid absorbent layers so that the liquid waste may not leak to the outside of the absorbent articles. For this purpose, there is an absorbent article which is provided on the surface of the liquid-receiving side with leakage preventing sidewalls extending longitudinally on the two widthwise sides.

In the general structure of the leakage preventing side walls of the prior art, a longitudinally extending unstretchable hydrophobic sheet is joined onto the top sheet of the absorbent article, and an elastic member extending longitudinally of the absorbent article is joined to the hydrophobic sheet. By the elastic shrinking force in the longitudinal direction of the elastic member, a curving force in the longitudinal direction is applied to the absorbent article, and the leakage preventing side walls are raised to the liquid-receiving side of the absorbent article so that the menstrual blood or the like may be prevented from leaking sideways.

In most of the leakage preventing side walls disposed in the absorbent article of the prior art, the elastic members are joined to the hydrophobic sheet while being extended generally in parallel with the liquid-receiving side surface of the absorbent article. When the absorbent article is worn on the crotch of a wearer, therefore, the leakage preventing side walls are indefinite whether they fall outward or inward in widthwise direction. While the absorbent article is worn, therefore, it frequently occurs that the leakage preventing side walls fall down inward in the widthwise direction of the absorbent article.

When the absorbent article is actually worn on the crotch of the wearer, the widthwise midway portion of the absorbent article is frequently deformed to bulge toward the skin of the wearer. If the leakage preventing side walls are fallen inward in the widthwise direction in such a deformed state, they are kept falling down while being in contact with the liquid-receiving side surface of the absorbent article, so that they scarcely restore their outward positions.

As a result, the leakage preventing side walls cannot function as the walls literally, so that the menstrual blood or urine given to the liquid-receiving surface of the absorbent article can not be stopped by the leakage preventing side walls, resulting in that the sideway leakage easily occurs to the sides of the absorbent article. When the leakage preventing side walls fall down inward in the widthwise direction, on the other hand, they cover the absorbing surface of the absorbent article so that the area of the region to contribute to the absorption of the liquid is restricted in the absorbent article.

In the absorbent article of the prior art, on the other hand, the elastic members disposed in the Leakage preventing side walls are extended in the longitudinal direction generally in parallel with the liquid-receiving side surface of the absorbent article. When the absorbent article is curved to conform to the front and rear shapes of the crotch, therefore, the leakage preventing side walls extending in the longitudinal direction are difficult to follow the shapes of the crotch. Therefore, the elastic members positioned at the longitudinal midway portion of the absorbent article abut excessively strongly against the crotch or the perineal portion so that the wearer easily feels a physical disorder.

SUMMARY OF THE INVENTION

The present invention has an object to provide an absorbent article in which leakage preventing side walls, when worn on the crotch of a wearer, can be easily directed outwardly in the widthwise direction so as to prevent sideway leakage of a liquid and also to prevent reduction in the substantial area of an absorbent region.

Another object of the invention is to provide an absorbent article in which leakage preventing side walls, when the absorbent article is worn on the crotch of a wearer and curved in accordance with the front and rear shapes of the crotch, can easily conform to the shapes of the crotch so as to prevent the leakage preventing side walls from giving a physical disorder to the wearer.

According to a first aspect of the invention, there is provided an absorbent article comprising: a main body including a support sheet, a liquid absorbent layer laid on the support sheet, and a liquid-permeable sheet covering the liquid absorbent layer; and leakage preventing side walls extending in the longitudinal direction of the main body and lying opposite one another in the widthwise direction of the main body, each leakage preventing side wall having a raised portion which is joined at a root end onto a liquid-receiving side surface of the main body and raised therefrom to have a free end positioned apart from the liquid-receiving side surface, wherein each leakage preventing side wall is provided with first elastically shrinking means for applying an elastic shrinking force along a shrinking action line approaching the free end from the root end as it extends from the two longitudinal end positions of the raised portion of the leakage preventing side wall toward the longitudinally midway position of the leakage preventing side wall.

In the above, when the leakage preventing side walls receives the pressure from the skin wearing the absorbent article, they are easily subjected to a force to bring them down outwardly in the widthwise direction. When the widthwise midway portion of the absorbent article is deformed to bulge toward the skin, therefore, the leakage preventing side walls easily contact with the skin to prevent the sideway leakage effectively. Since the leakage preventing side walls hardly fall down inwardly, moreover, the substantial absorbing area of the liquid-receiving side surface is hardly reduced.

According to a second aspect of the invention, there is provided an absorbent article comprising: a main body including a support sheet, a liquid absorbent layer laid on the support sheet, and a liquid-permeable sheet covering the liquid absorbent layer; and leakage preventing side walls extending in the longitudinal direction of the main body and lying opposite one another in the widthwise direction of the main body, each leakage preventing side wall having a raised portion which is joined at a root end onto a liquid-receiving side surface of the main body and raised therefrom to have a free end positioned apart from the liquid-receiving side surface, wherein each leakage preventing side wall is provided with first elastically shrinking means for applying an elastic shrinking force along a shrinking action line approaching the root end from the free end as it extends from the two longitudinal end positions of the raised portion of the leakage preventing side wall toward the longitudinally midway position of the leakage preventing side wall.

In the above, when the absorbent article is worn on the crotch of a wearer's body, the leakage preventing side walls are easily deformed to conform to the front and rear curved shapes of the crotch to improve their contact with the skin. Moreover, the leakage preventing side walls can be prevented from abutting excessively strongly against the perineal region or the like.

In the above absorbent articles according to the first and second aspects of the invention, it is preferred that the shrinking action line is curved outwardly or inwardly as it extends toward the longitudinally midway position. However, the shrinking action line may extend generally into such a V-shape that it is folded at the longitudinally midway position to have two strictly or generally straight line portions extending therefrom.

Preferably, the leakage preventing side wall is provided with second elastically shrinking means for applying an elastic shrinking force in the longitudinal direction along the free end. However, it may be possible that elastically shrinking means is not disposed at the free end.

Preferably, the leakage preventing side wall has front and rear end portions longitudinally outwardly of the raised portion, and the front and rear end portions are folded substantially flat and joined onto the main body with the free end being directed outwardly in the widthwise direction.

It may be possible that the leakage preventing side wall is provided with third elastically shrinking means for applying an elastic shrinking force in the longitudinal direction, the third elastically shrinking means being located between the shrinking action line and the root end, that the leakage preventing side wall has front and rear end portions longitudinally outwardly of the raised portion, and that the front and rear end portions are folded substantially flat and joined onto the main body with the free end and the portion having the third elastically shrinking means being directed outwardly in the widthwise direction.

If the front and rear end portions of the leakage preventing side walls are thus folded with the free ends being directed outwardly in the widthwise direction, the free ends of the raised portions of the leakage preventing side walls can be easily directed outwardly in the widthwise direction. When the absorbent article is worn, therefore, the raised portions of the leakage preventing side walls easily fall down outwardly in the widthwise direction and easily come into close contact with the wearer's skin at the portions between the shrinking action lines and the free ends.

It is possible that the individual elastically shrinking means are each formed by attaching a linear or band-shaped elastic member to a side wall sheet forming the leakage preventing side wall. In this case, a single elastic member may be provided to extend continuously, or a plurality of elastic members may be provided at an interval. Alternatively, the side wall sheet forming the leakage preventing side wall may be provided in itself with an elastically shrinking function to form the individual shrinking action lines. For example, the elastically shrinking means may be formed by forming folding lines (or creases) along the curved shrinking action lines in the side wall sheet exhibiting the shrinkability in the longitudinal direction or by stitching elastic members for forming the shrinking action lines in the nonstretchable side wall sheet.

DESCRIPTION OF THE PREFERRED EMBODIMENTS

Figure 1:
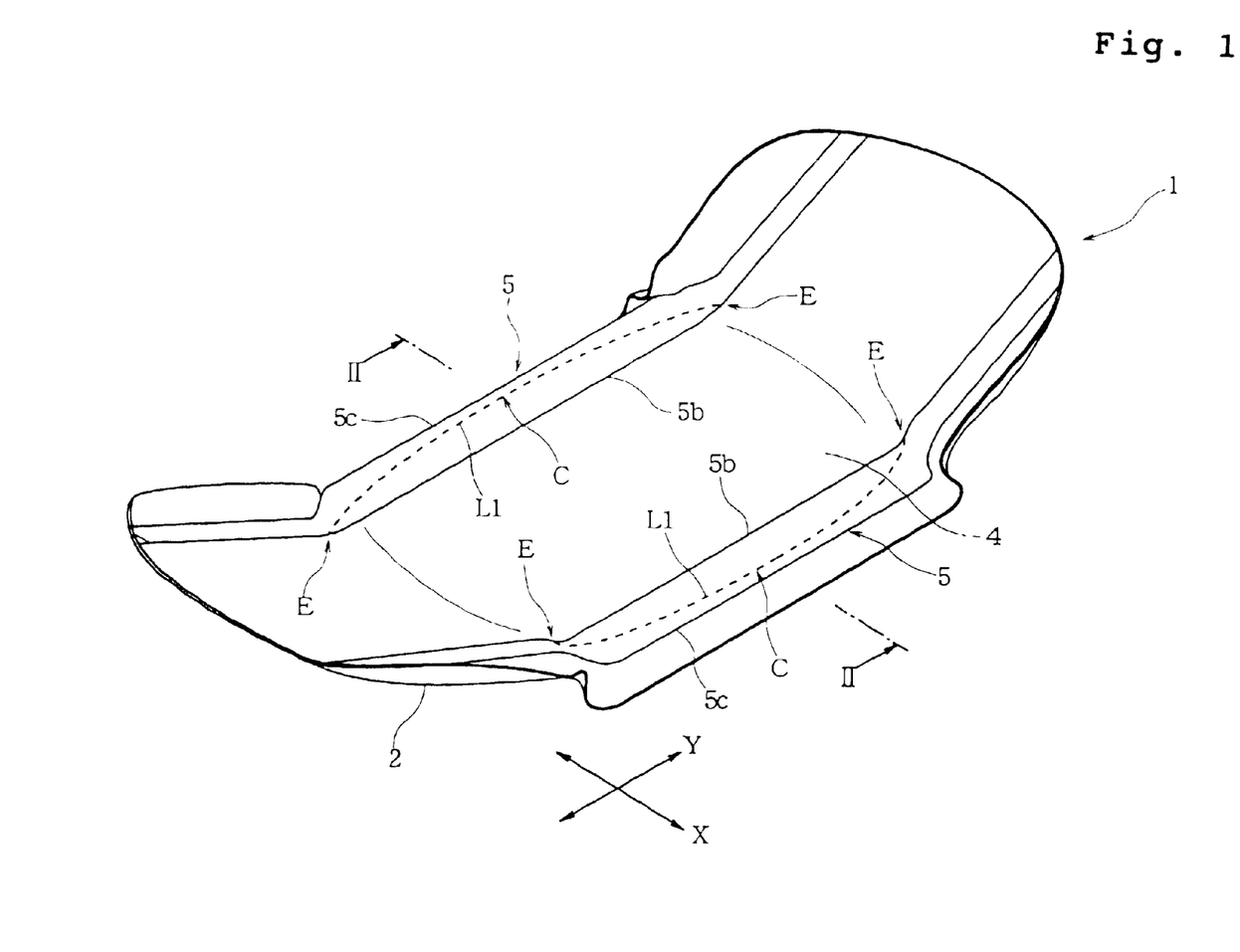
FIG. 1 is a perspective view showing a sanitary napkin as an absorbent article according to a first embodiment of the invention.
Figure 2:
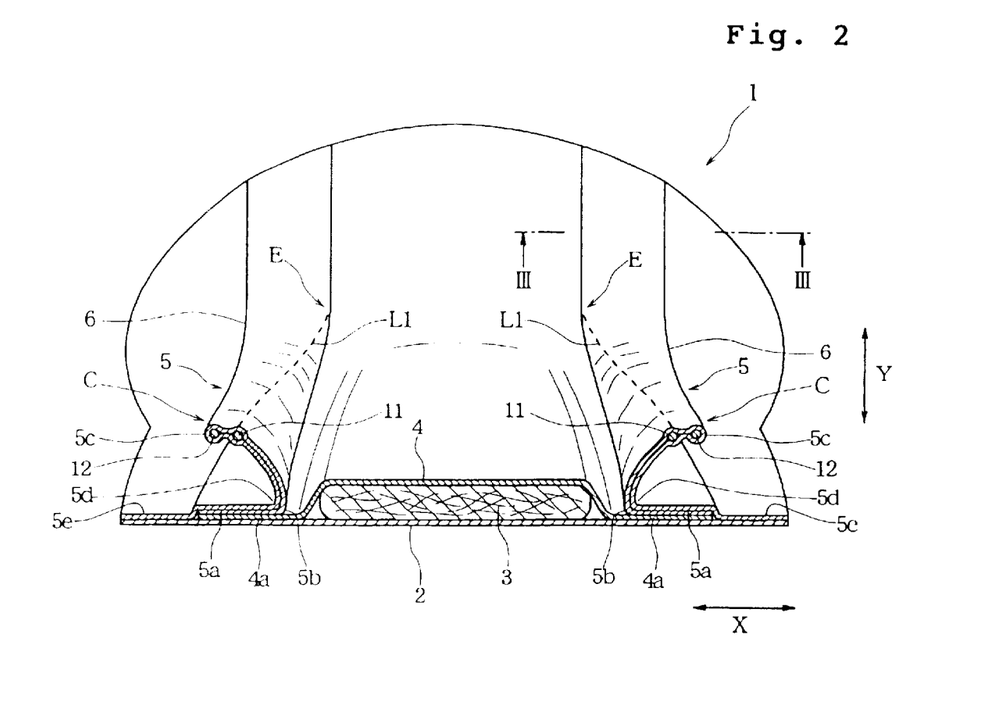
FIG. 2 is a sectional view of the sanitary napkin shown in FIG. 1 and taken along line II—II.

The invention will be described with reference to the accompanying drawings. FIG. 1 is a perspective view showing a sanitary napkin 1 as an absorbent article according to a first embodiment of the invention and taken from a liquid-receiving side; FIG. 2 is a sectional view taken along line II—II of FIG. 1; and FIG. 3 is an enlarged sectional view of a portion taken along line III—III of FIG. 2.

Figure 3:
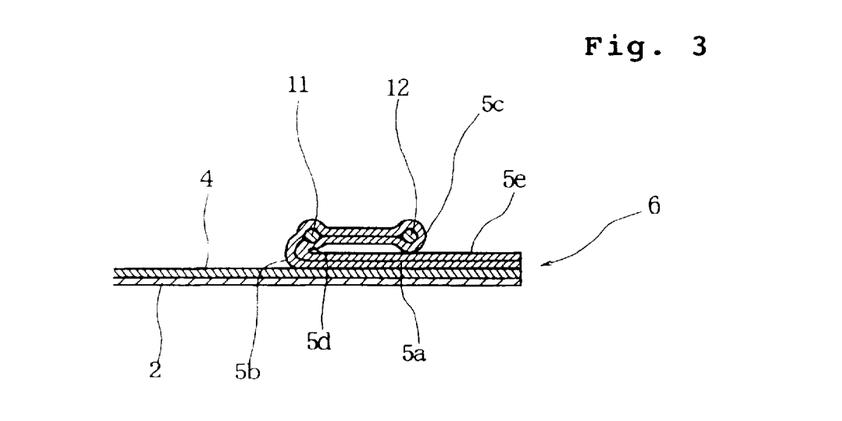
FIG. 3 is an enlarged sectional view of a portion taken along line III—III of FIG. 2.

The sanitary napkin 1, as shown in FIGS. 1 to 3, has a main body including: a support sheet 2 for confronting an external wear such as underwear; a liquid absorbent layer 3 laid on the wearer side of the support sheet 2 and positioned at the midway portion thereof in the widthwise direction (or in the X direction) for absorbing a liquid waste; and a liquid-permeable sheet 4 for covering the liquid-receiving side surface of the liquid absorbent layer 3. The liquid-permeable sheet 4 has two side end portions 4a, which are extended outwardly of the liquid absorbent layer 3 in the widthwise direction (or in the X direction), and are joined to the surface of the support sheet 2.

On two side portions of the main body of the sanitary napkin 1 lying opposite one another in the widthwise direction (or in the X direction), there are disposed a pair of leakage preventing side walls 5 and 5 which are extended in the longitudinal direction (or in the Y direction). In this embodiment, the individual leakage preventing side walls 5 are formed of one side wall sheet 6.

The side wall sheet 6 is formed of a hydrophobic nonwoven fabric or a hydrophobic resin film. The leakage preventing side wall 5 has a two-layered structure in which the side wall sheet 6 is folded to have inner and outer folded portions laminated one another. These inner and outer folded portions are fixed on the side end portion 4a of the liquid-permeable sheet 4, individually at root ends 5b and 5d, and are extended away from the support sheet 2 to form a free end 5c. Namely, the side wall sheet 6 is folded at the free end 5c. The rest of the side wall sheet 6, i.e., the portions not forming the leakage preventing side wall 5 are extended along and fixed on the surface of the main body. In FIG. 2, the portion 5a extending outwardly of the root end 5b is fixed on the side end portion 4a of the liquid-permeable sheet4; the portion 5e extending outwardly of the root end 5d is fixed on the side end portion 4a of the liquid-permeable sheet4 (through the portion 5a) and on the support sheet 2.

It should be noted that the leakage preventing side wall 5 rises from the main body only at a portion between positions E and E, but does not rise from the main body at front and rear end portions outside of the positions E and E. More specifically, as shown in FIG. 3, the front and rear end portions of the leakage preventing side wall 5 fall flat to and are fixed on the surface of the main body as a whole. At this time, the free end 5c of the leakage preventing side wall 5 is directed outwardly in the widthwise direction (or the X direction).

In the leakage preventing side wall 5, a first elastic member 11 is sandwiched between and joined to the inner and outer folded portions of the side wall sheet 6. This first elastic member 11 provides elastically shrinking means for applying a shrinking force to the leakage preventing side wall 5 along a line indicated at L1. This line L1 along which the shrinking force by the first elastic member 11 acts is referred to in this specification as "a shrinking action line L1".

As shown in FIGS. 1 and 2, the shrinking action line L1 is curved. At the positions E and E indicating the longitudinal ends of the raised portion of the leakage preventing side wall 5, the shrinking action line L1 is substantially aligned with the root end (5b and 5d) of the leakage preventing side wall 5. At the position C indicating the longitudinally midway position of the leakage preventing side wall 5, on the other hand, the shrinking action line L1 is positioned in the vicinity of the free end 5c of the leakage preventing side wall 5. Alternatively, it is also possible that the shrinking action line L1 is positioned in the vicinity of the root end (5b and 5) at the end positions E and E, while being substantially aligned with or being positioned in the vicinity of the free end 5c at the midway position C.

In the invention, the midway position C need not be located at the longitudinally strict center position of the raised portion of the leakage preventing side wall 5 but can be set at an arbitrary position between the two end positions E and E. In short, the shrinking action line L1 extends to closely approach the free end 5c at any position between the two ends E and E.

In the embodiment shown, the single elastic member 11 extends continuously all along the shrinking action line L1. However, a plurality of elastic members may be provided at an interval to extend intermittently along the shrinking action line L1.

At the free end 5c of the leakage preventing side wall 5, as shown in FIG. 2, a second elastic member 12 is joined to the inner side of the folded-back portion of the side wall sheet 6. This second elastic member 12 also provides elastically shrinking means for applying a shrinking force to the leakage preventing side wall 5 along a line substantially aligned with the free end 5c. Hereinafter, this line along which the shrinking force by the second elastic member 12 acts is referred to as "a free end-side shrinking action line". This second elastic member 12 extends continuously all over the length of the free end 5c. However, a plurality of elastic members may be provided at an interval to extend intermittently along the free end 5c.

Since the shrinking action line L1 is curved, as described hereinbefore, the first elastic member 11 forming the shrinking action line L1 and the second elastic member 12 forming the free end-side shrinking action line are spaced from each other at the two end positions E and E of the raised portion of the leakage preventing side wall 5 but are located closer to each other at the midway position C. Here, the first and second elastic members 11 and 12 may be in contact with or overlapped with each other at the midway position C.

In the embodiment shown, moreover, the first and second elastic members 11 and 12 are extended from the raised portion farther to the front and rear end portions of the leakage preventing side wall 5, as shown in FIG. 3. In the front and rear end portions, the first and second elastic members 11 and 12 are spaced from each other, as in the two end positions E and E.

At the front and rear end portions of the sanitary napkin 1 in the longitudinal direction (or in the Y direction), as described hereinbefore, the leakage preventing side wall 5 is joined to the liquid-receiving side surface. In the free state where the sanitary napkin 1 is not worn, therefore, the sanitary napkin 1 is so curved that the liquid-receiving side is recessed by the elastic shrinking forces of the first elastic member 11 and the second elastic member 12 and that the leakage preventing side wall 5 rises at its free end 5c away from the support sheet 2. Moreover, since the leakage preventing side wall 5 is fallen and joined as a whole at its front and rear end portions to the main body while having its free end 5c being directed outward, as shown in FIG. 3, the leakage preventing side wall 5 rises so obliquely in the portion between the end positions E and E (or the raised portion) that its free end 5c is directed outwardly in the widthwise direction with respect to the root ends 5b and 5d.

Here, at any position of the raised portion (i.e., the portion between the end positions E and E) of the leakage preventing side wall 5, the shrinking tension to be exhibited by the second elastic member 12 disposed on the side of the free end 5c is preferred to be stronger than the component, as taken in the Y direction, of the shrinking tension of the first elastic member 11 forming the shrinking action line L1. With this construction, in the free state where the sanitary napkin 1 is not worn, the free end 5c of the leakage preventing side wall 5 can farther leave the support sheet 2 than the portion where the shrinking action line L1 extends, so that the portion between the shrinking action line L1 and the free end 5c ascends outwardly in the widthwise direction from the support sheet 2.

In the free state of the sanitary napkin 1, as shown in FIGS. 1 and 2, the individual leakage preventing side walls 5 and 5 are raised and inclined outwardly in the widthwise direction, and the shrinking action lines L1 are so curved as are positioned closer to the root ends (5b and 5d) at the end positions E and as are positioned closer to the free ends 5c at the midway positions C. In the free state, therefore, the leakage preventing side walls 5 take a three-dimensional stereoscopic structure conforming to the shape of the crotch such as the perineal region.

Figure 11:
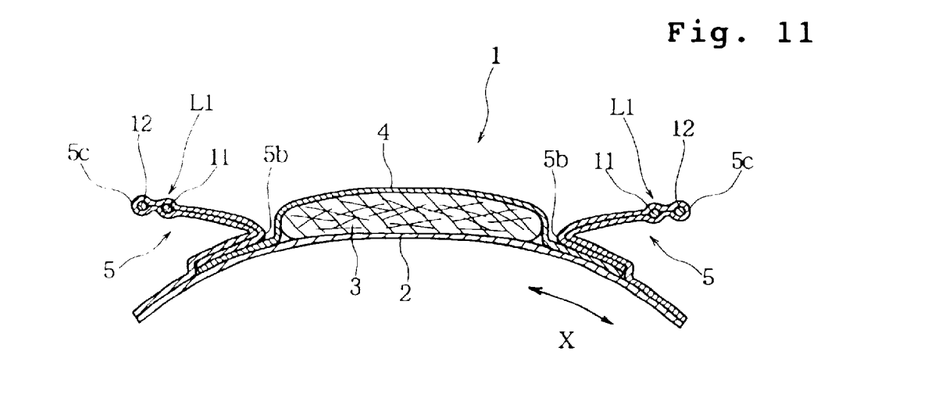
FIG. 11 is a widthwise sectional view showing the state in which the sanitary napkin is worn.

FIG. 11 is a sectional view showing the state where the sanitary napkin 1 is worn on the crotch of the wearer's body (not shown). When the sanitary napkin 1 is worn on the crotch, the portions having the free ends 5c and the shrinking action lines L1 of the raised portions (i.e., the portions between E and E) of the leakage preventing side walls 5 abut against the skin so that those portions are subjected to pressures toward the support sheet 2 by the pressure coming from the external wear such as the underwear. At this time, the raised portions of the leakage preventing side walls 5 can be easily fallen away from each other (or outwardly in the widthwise direction) due to the curved shapes of the shrinking action lines L1.

In the state where the sanitary napkin 1 is worn on the crotch, on the other hand, the pressure coming from the external wear highly acts on the widthwise central portion of the sanitary napkin 1 so that the sanitary napkin 1 is easily deformed to bulge toward the skin of the wearer's body at the widthwise central portion thereof. In this deformed state, the leakage preventing side walls 5 and 5 fall hardly toward the liquid absorbent layer 3 but easily outwardly in the widthwise direction, as shown in FIG. 11. Therefore, the leakage preventing side walls 5 and 5 are prevented from falling down on the liquid absorbing surface of the sanitary napkin 1. This results in preventing reduction of the substantial area of the liquid absorbing surface.

Moreover, the leakage preventing side walls, as having fallen outwardly in the widthwise direction, can easily come into close contact with the perineal region, at the portions between the curved shrinking action lines L1 and the free ends 5c. Therefore, the contact between the leakage preventing side walls 5 and the wearer's skin can be enhanced to keep the sideway leakage preventing effect high.

Figure 4:
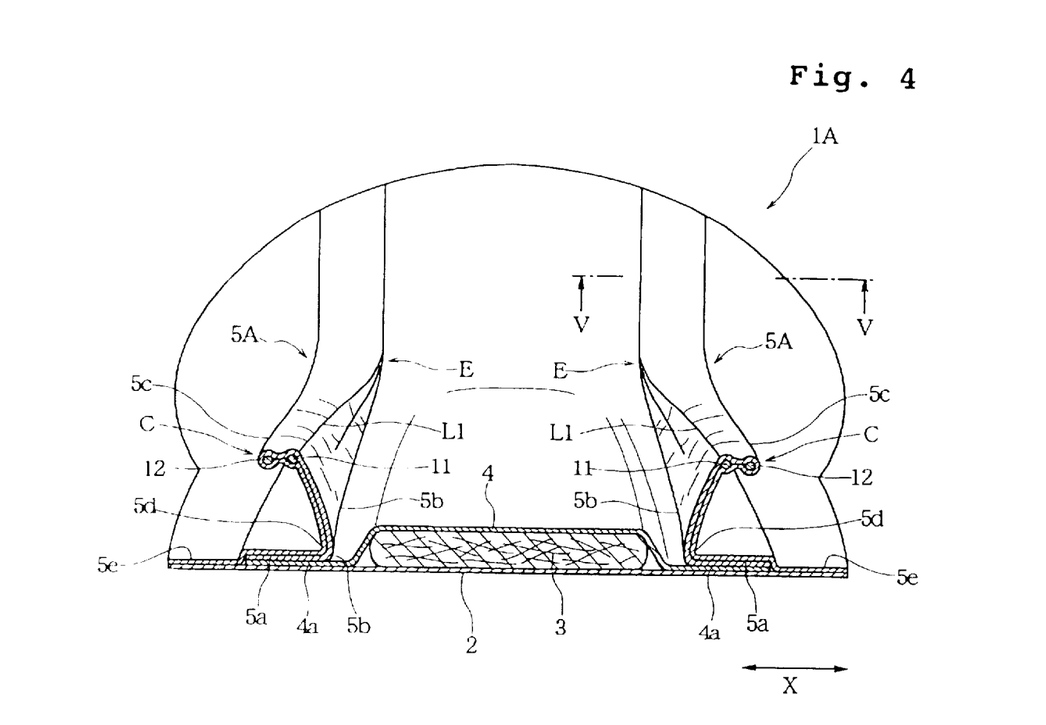
FIG. 4 is a sectional view showing a modification of the sanitary napkin shown in FIG. 1.
Figure 5:
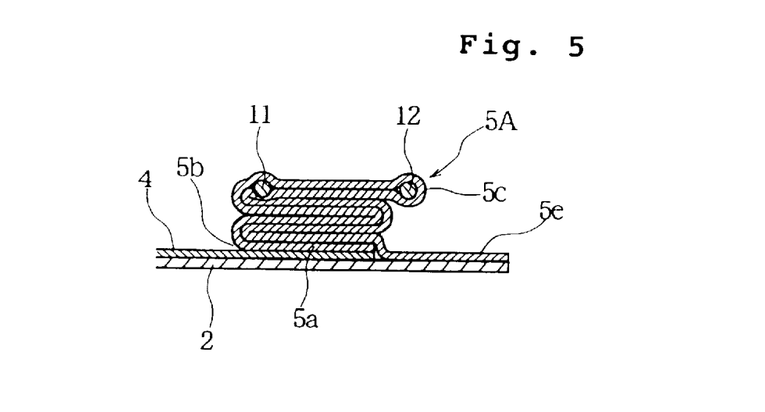
FIG. 5 is an enlarged sectional view of a portion taken along line V—V of FIG. 4.

FIG. 4 is a sectional view similar to that of FIG. 2 but shows a sanitary napkin 1A as a modification of the first embodiment of the invention, and FIG. 5 is an enlarged sectional view of a portion taken along line V—V of FIG. 4.

The sanitary napkin 1A shown in FIGS. 4 and 5 has almost the same construction as that shown in FIG. 2, except that the folding structure of leakage preventing side walls 5A at the front and rear end portions of the sanitary napkin 1A is different from that shown in FIG. 3.

Hereinafter, the detailed description of the portions having the same constructions as those of the first embodiment will be omitted by designating them by the common reference numerals.

In this embodiment, at the front and rear end portions, the leakage preventing side wall 5A is folded along three folding lines and is joined to the upper surface of the liquid-permeable sheet 4, as shown in FIG. 5. In this structure, too, the free end 5c is directed outward in the widthwise direction.

In the free state where the sanitary napkin 1A is not worn on the wearer's body, since the leakage preventing side wall 5A is folded along the three folding lines at the front and rear end portions, the portion between E and E (or the raised portion) of the leakage preventing side wall 5A can rise with the portion between the root end (5b and 5d) and the shrinking action line L1 being at an angle closer to a right angle from the liquid-permeable sheet 4, as compared with that shown in FIG. 2. When the sanitary napkin 1A is worn on the wearer's body, therefore, the portion having the curved shrinking action line L1 can abut preferentially against the perineal region.

Figure 6:
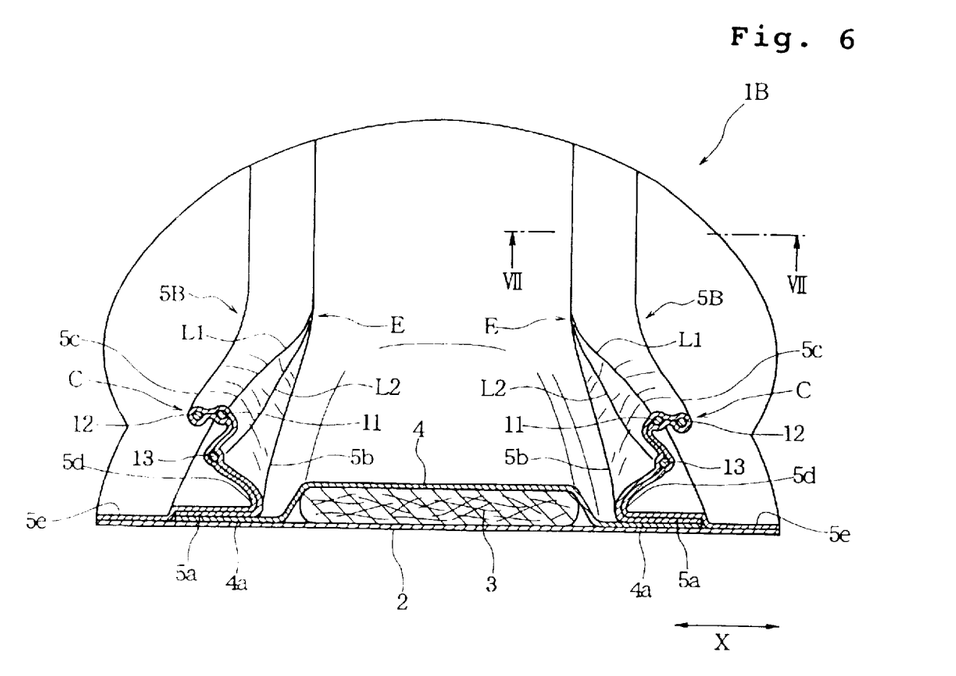
FIG. 6 is a sectional view showing another modification.
Figure 7:
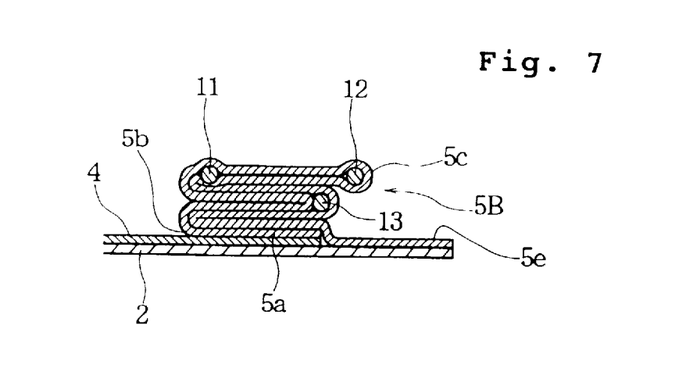
FIG. 7 is an enlarged sectional view of a portion taken along line VII—VII of FIG. 6.

FIG. 6 is a sectional view similar to that of FIG. 2 but shows a sanitary napkin 1B as another modification of the first embodiment, and FIG. 7 is an enlarged sectional view of a portion taken along line VII—VII of FIG. 6.

The sanitary napkin 1B has almost the same construction as that shown in FIG. 2, except for leakage preventing side walls 5B. The folding structure of the leakage preventing side walls 5B at the front and rear end portions is identical to that shown in FIG. 5.

In the sanitary napkin 1B shown in FIGS. 6 and 7, however, another elastic member (or a third elastic member) 13 is joined to the intermediate portion between the first elastic member 11 forming the shrinking action line L1 and the root end (5b and 5d) of the leakage preventing side wall 5B. This third elastic member 13 also forms elastically shrinking means for exhibiting a shrinking force in the longitudinal direction. By this elastically shrinking means, there is formed an intermediate portion-side shrinking action line L2 which is located between the shrinking action line L1 and the root end (5b and 5d) and is extended in the longitudinal direction generally in parallel with the free end 5c.

As shown in FIG. 7, moreover, the leakage preventing side wall 5B is so folded at the front and rear end portions of the sanitary napkin 1B that the portion provided with the third elastic member 13 is directed outwardly in the widthwise direction, as at the free end 5c.

In this embodiment, as shown in FIG. 6, the leakage preventing side wall 5B in the free state rises at the portion between E and E into such a zigzag sectional shape that the portion provided with the third elastic member 13 is located on the outer side in the widthwise direction than the shrinking action line L1 and the root end (5b and 5d).

Therefore, the rising wall from the root end (5b and 5d) to the portion having the shrinking action line L1 easily rises over the liquid-permeable sheet 4 at an angle close to the right angle. When the sanitary napkin 1B is worn on the crotch of the wearer's body, the portion having the shrinking action line L1 easily abuts against the perineal region, and the portion between the shrinking action line L1 and the free end 5c easily contacts with the perineal region.

Figure 8:
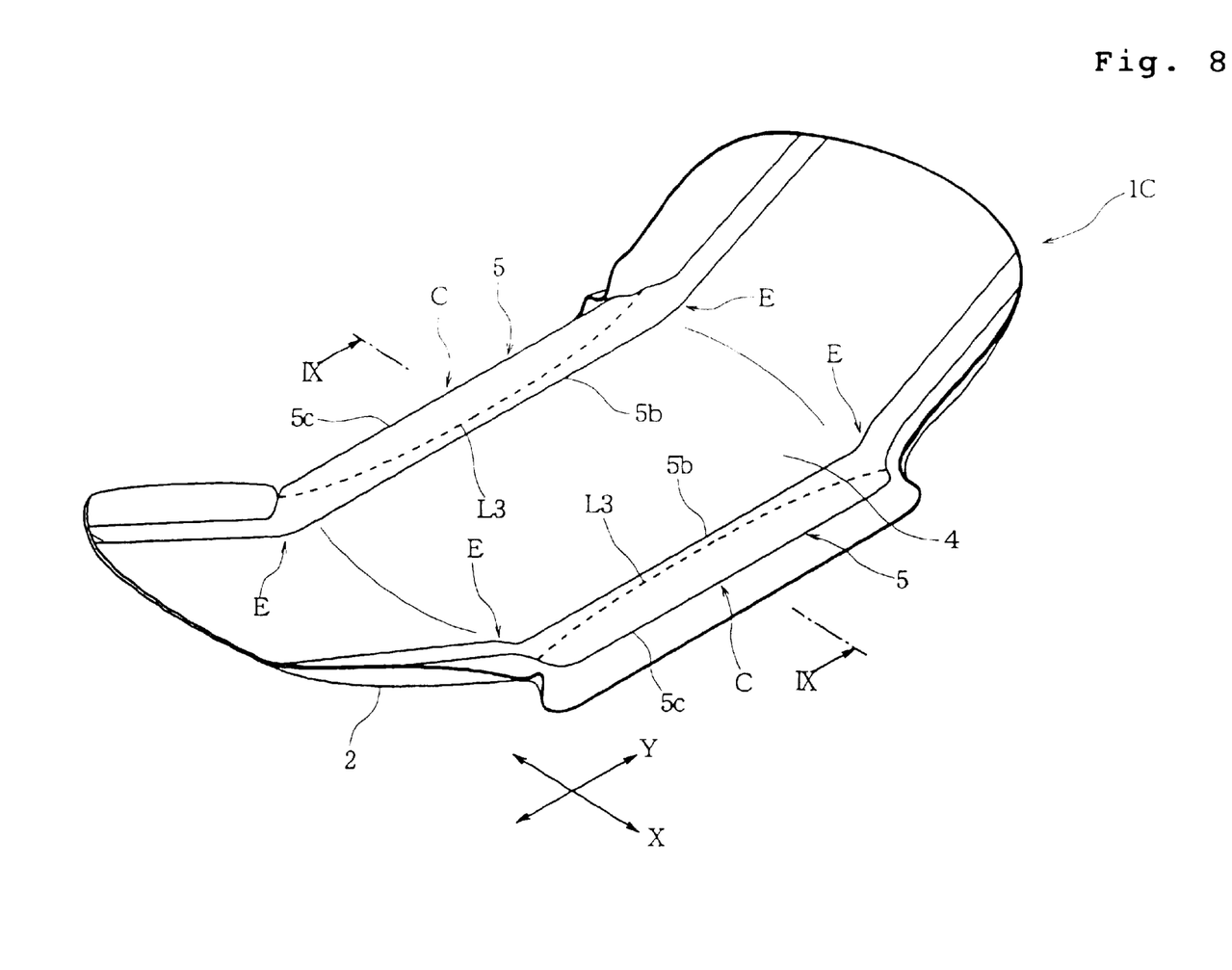
FIG. 8 is a perspective view showing a sanitary napkin as an absorbent article according to a second embodiment of the invention.
Figure 9:
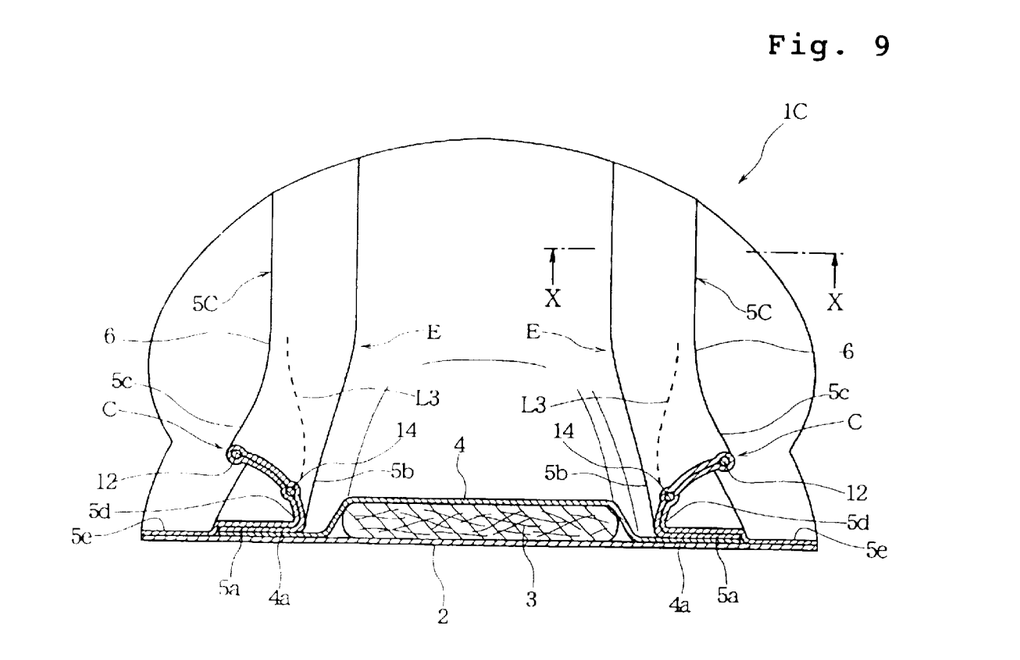
FIG. 9 is a sectional view taken along line IX—IX of FIG. 8.

FIG. 8 is a perspective view showing a sanitary napkin 1C according to a second embodiment of the invention; FIG. 9 is a sectional view taken along line IX—IX of FIG. 8; and FIG. 10 is an enlarged sectional view of a portion taken along line X—X of FIG. 9.

Figure 10:
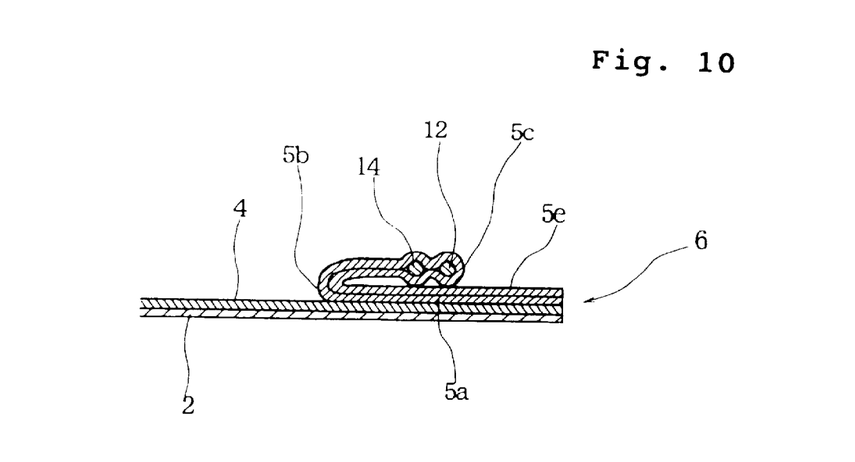
FIG. 10 is an enlarged sectional view of a portion taken along line X—X of FIG. 9.

The sanitary napkin 1C shown in FIGS. 8 to 10 has almost the same construction as that shown in FIG. 2, except for leakage preventing side walls 5C. The folding structure of the leakage preventing side wall 5C at the front and rear end portions of the sanitary napkin 1C is identical to that shown in FIG. 3.

In the sanitary napkin 1C shown in FIGS. 8 to 10, there is also provided the second elastic member 12 along the free end 5c. Between the free end 5c and root end (5b and 5d), however, provided is an elastic member 14, in place of the first elastic member 11. This elastic member 14 forms a shrinking action line L3, which is located in the vicinity of the free end 5c at the two end positions E and E of the raised portion of the leakage preventing side wall 5c but is curved to approach the root end (5b and 5d) as extending toward the midway position C.

In other words, the shrinking action line L3 extends to approach the root end (5b and 5d) closer at the midway position C than at the end positions E so that it has a curved shape reversed from that of the sanitary napkin 1 shown in FIG. 1.

At the two end positions E and E, the elastic member 14 is positioned closer to the second elastic member 12 provided in the free end 5c. At the midway position C, the elastic member 14 is positioned closer to the root end (5b and 5d). Alternatively, it is also possible that the elastic member 14 contacts with or overlaps with the second elastic member 12 at the end positions E and E and/or that the elastic member 14 is substantially aligned with the root end (5b and 5d) at the midway position C.

The elastic member 14 is extended all over the length of the shrinking action line L3. Alternatively, a plurality of elastic members may be provided at an interval to extend intermittently along the shrinking action line L3. It is preferred that the shrinking tension of the second elastic member 12 provided on the side of the free end 5c is higher than that of the elastic member 14.

In the sanitary napkin 1C thus constructed, the leakage preventing side walls 5C and 5C rise individually at the portions between E and E in which the shrinking action line L3 is so curved as to sink at the midway position C toward the liquid-permeable sheet 4.

Figure 12:
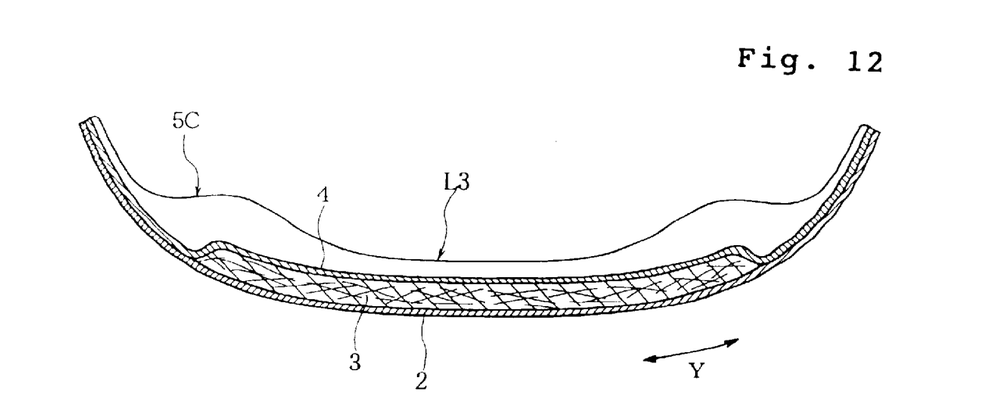
FIG. 12 is a longitudinal sectional view showing the state in which the sanitary napkin is worn.

In the state where the sanitary napkin 1C is worn on the wearer's crotch, as shown in FIG. 12, the leakage preventing side walls 5C and 5C easily take such a three-dimensional stereoscopic shape as is contoured to conform generally to the shape of the crotch curved in a direction from the front to the rear of the wearer's body.

When the sanitary napkin 1C is worn on the crotch of the wearer's body, therefore, the leakage preventing side walls 5c can easily contact with the skin of the crotch over a long range in the direction from the front to the rear of the wearer's body, at the portions between the shrinking action lines L3 and the free ends 5c. Especially at the midway positions C, the shrinking action line L3 and the free end 5c are spaced away from each other so largely that the leakage preventing side walls 5c easily come into close contact with the perineal region at these positions. Therefore, the leakage preventing side walls 5C and 5C can prevent the sideway leakage effectively.

In the foregoing individual embodiments, the width size from the root end (5b and 5d) to the free end 5c of the leakage preventing side wall is preferred to be within a range of 5 mm to 20 mm.

The side wall sheet 6 is hydrophobic or water-repellent and is formed of a melt-blown nonwoven fabric, an air-through nonwoven fabric, a point-bonded nonwoven fabric, an air-laid nonwoven fabric, or a composite nonwoven fabric having a spun-bonded nonwoven fabric and a melt-blown nonwoven fabric adhered to each other. Alternatively, the side wall sheet 6 may be formed of a resin film or a laminate material of a nonwoven fabric and a resin film. The nonwoven fabric may be made of fibers of PE (polyethylene), PP (polypropylene) or PET (polyethylene terephthalate), or composite synthetic fibers such as those of PE/PP or PE/PET, e.g., the core-sheath type fibers or side-by-side type fibers.

The elastic members 11, 12, 13 and 14, as attached to the leakage preventing side walls, can be formed of natural rubber, synthetic rubber, polyurethane or styrene-butadiene copolymer to take a shape of yarns, filaments, film or band (or belt). Alternatively, the elastic members 11, 12, 13 and 14 may be prepared by cutting a stretchable nonwoven fabric such as an elastic spun-bonded nonwoven fabric or an elastic melt-blown nonwoven fabric.

The individual elastic members 11, 12, 13 and 14 are attached to the leakage preventing side walls with an adhesive, etc., while being elongated (or stretched) by about 1.1 to 2 times.

The support sheet 2 is preferably formed of a liquid-impermeable sheet. This support sheet 2 is exemplified by an air-permeable resin film, a spun-bonded or spun-laced non-woven fabric made water-repellent, or a laminate material prepared by joining an air-permeable resin film onto the back of a nonwoven fabric. Here, the support sheet 2 is preferably provided on its back with an adhesive layer for retaining the sanitary napkin to the external wear such as the underwear, and a release sheet for protecting the adhesive layer till the sanitary napkin is used.

The liquid-permeable sheet 4 is formed of a nonwoven fabric made of PE fibers, PP fibers, PET fibers or their composite fibers subjected to a hydrophilic treatment, such as a spun-bonded nonwoven fabric or a spun-laced nonwoven fabric. Alternatively, an opened (or porous) resin sheet may be employed to form the liquid-permeable sheet 4.

The liquid absorbent layer 3 is formed of pulverized pulp or a mixture of pulverized pulp and a highly water-absorbing polymer (or super absorbent polymer), by enveloping either the pulverized pulp or the mixture of the pulverized pulp and the highly water-absorbing polymer by an absorbent sheet such as tissue.

Although the invention has been described on the embodiments in which the absorbent article is exemplified by the sanitary napkin, the present invention can also be applied to a disposable diaper, a urine absorbing pad, or any other absorbent articles.

According to the invention thus far described in detail, the leakage preventing side walls can easily fall outwardly and contact with the perineal region when the sanitary napkin is worn on the crotch of the wearer's body. Alternatively, the leakage preventing side walls can be so easily deformed according to the shape of the crotch curved in the direction from the front to the rear of the wearer's body as to contact with the perineal region. On the other hand, the leakage preventing side walls hardly abut strongly against the skin of the wearer to provide an excellent wearing feel.

Although various exemplary embodiments have been shown and described, the invention is not limited to the embodiments shown. Therefore, the scope of the invention is intended to be limited solely by the scope of the claims that follow.

What is claimed is:

1. An absorbent article comprising:
   a main body including a support sheet, a liquid absorbent layer laid on said support sheet, and
   a liquid-permeable sheet covering said liquid absorbent layer; and leakage preventing side walls extending in a longitudinal direction of said main body and lying opposite one another in a latitudinal direction of said main body, each leakage preventing side wall having a raised portion which is joined at a root end onto a liquid-receiving side surface of said main body and raised therefrom to have a free end positioned apart from the liquid-receiving side surface,
   wherein each leakage preventing side wall is provided with first elastically shrinking means for applying an elastic shrinking force along a curved shrinking action line that approaches said free end from said root end when extending from two longitudinal end positions of said raised portion of said leakage preventing side wall toward a longitudinally midway position of said leakage preventing side wall.

2. The absorbent article as set forth in claim 1, wherein said curved shrinking action line curves outwardly when extending toward said longitudinally midway position.

3. The absorbent article as set forth in claim 2,
   wherein said leakage preventing side wall is provided with second elastically shrinking means for applying an elastic shrinking force in the longitudinal direction along said free end.

4. The absorbent article as set forth in claim 3,
   wherein said leakage preventing side wall has front and rear end portions extending longitudinally outwardly of said raised portion, and said front and rear end portions are folded substantially flat and joined onto said main body with said free end being directed outwardly in the latitudinal direction.

5. The absorbent article as set forth in claim 4, wherein said first and second elastically shrinking means are each formed by attaching a linear or band-shaped elastic member to a side wall sheet forming said leakage preventing side wall.

6. The absorbent article as set forth in claim 3, wherein said leakage preventing side wall is provided with third elastically shrinking means for applying an elastic shrinking force in the longitudinal direction, said third elastically shrinking means being located between said shrinking action line and said root end, and wherein said leakage preventing side wall has front and rear end portions extending longitudinally outwardly of said raised portion, and said front and rear end portions are folded substantially flat and joined onto said main body with said free end and the portion having said third elastically shrinking means being directed outwardly in the latitudinal direction.

7. The absorbent article as set forth in claim 6, wherein said first, second and third elastically shrinking means are each formed by attaching a linear or band-shaped elastic member to a side wall sheet forming said leakage preventing side wall.

8. An absorbent article comprising:

a main body including a support sheet, a liquid absorbent layer laid on said support sheet, and a liquid-permeable sheet covering said liquid absorbent layer; and leakage preventing side walls extending in a longitudinal direction of said main body and lying opposite one another in a latitudinal direction of said main body, each leakage preventing side wall having a raised portion which is joined at a root end onto a liquid-receiving side surface of said main body and raised therefrom to have a free end positioned apart from the liquid-receiving side surface, wherein each leakage preventing side wall is provided with first elastically shrinking means for applying an elastic shrinking force along a curved shrinking action line that approaches said root end from said free end when extending from two longitudinal end positions of said raised portion of said leakage preventing side wall toward a longitudinally midway position of said leakage preventing side wall.

9. The absorbent article as set forth in claim 8, wherein said curved shrinking action line curves inwardly when extending toward said longitudinally midway position.

10. The absorbent article as set forth in claim 9, wherein said leakage preventing side wall is provided with second elastically shrinking means for applying an elastic shrinking force in the longitudinal direction along said free end.

11. The absorbent article as set forth in claim 10, wherein said leakage preventing side wall has front and rear end portions extending longitudinally outwardly of said raised portion, and said front and rear end portions are folded substantially flat and joined onto said main body with said free end being directed outwardly in the latitudinal direction.

12. The absorbent article as set forth in claim 11, wherein said first and second elastically shrinking means are each formed by attaching a linear or band-shaped elastic member to a side wall sheet forming said leakage preventing side wall.

13. The absorbent article as set forth in claim 10, wherein said leakage preventing side wall is provided with third elastically shrinking means for applying an elastic shrinking force in the longitudinal direction, said third elastically shrinking means being located between said shrinking action line and said root end, and wherein said leakage preventing side wall has front and rear end portions extending longitudinally outwardly of said raised portion, and said front and rear end portions are folded substantially flat and joined onto said main body with said free end and the portion having said third elastically shrinking means being directed outwardly in the latitudinal direction.

14. The absorbent article as set forth in claim 13, wherein said first, second and third elastically shrinking means are each formed by attaching a linear or band-shaped elastic member to a side wall sheet forming said leakage preventing side wall.

* * * * *